United States Patent [19]

Hunger et al.

[11] Patent Number: 4,716,103

[45] Date of Patent: Dec. 29, 1987

[54] CHEMICALLY ACTIVE TRIAZINE SUPPORT COMPOSITION

[75] Inventors: Hans-Dieter Hunger, Zepernick; Charles Coutelle, Berlin, both of German Democratic Rep.

[73] Assignee: Akademie der Wissenschaften der DDR, Berlin, German Democratic Rep.

[21] Appl. No.: 638,882

[22] Filed: Aug. 8, 1984

[30] Foreign Application Priority Data

| Aug. 9, 1983 | [DD] | German Democratic Rep. ... 253821 |
| Apr. 24, 1984 | [DD] | German Democratic Rep. ... 262260 |
| Apr. 24, 1984 | [DD] | German Democratic Rep. ... 262265 |
| Apr. 24, 1984 | [DD] | German Democratic Rep. ... 262264 |
| Apr. 24, 1984 | [DD] | German Democratic Rep. ... 262263 |
| Apr. 24, 1984 | [DD] | German Democratic Rep. ... 262261 |

[51] Int. Cl.$^4$ ............ C12Q 1/68; C12N 11/12; G01N 33/544; C07D 251/00
[52] U.S. Cl. ............ 435/5; 422/68; 435/6; 435/174; 435/179; 436/530; 530/814; 536/56; 544/180; 544/190
[58] Field of Search ............ 435/174, 179, 180, 181, 435/5, 6; 536/56; 436/530; 544/180, 190; 260/112 R; 422/68; 530/814

[56] References Cited

U.S. PATENT DOCUMENTS

| 3,619,371 | 11/1971 | Crook et al. ........................ 435/179 |
| 3,674,767 | 7/1972 | Lilly et al. ...................... 435/179 X |
| 3,824,150 | 7/1974 | Lilly et al. ...................... 435/179 X |
| 4,229,537 | 10/1980 | Hodgins et al. ................. 435/181 X |
| 4,357,311 | 11/1982 | Schutt ............................... 436/530 |

FOREIGN PATENT DOCUMENTS

52-983  4/1977  Japan .................................. 435/181

*Primary Examiner*—David M. Naff
*Attorney, Agent, or Firm*—Michael J. Striker

[57] ABSTRACT

A support composition based on triazine derivatives is prepared having high binding capacity. The support composition contains a polymer compound having no triazine groups, a polymer compound with 4,6-dihalogen-1,3,5-triazine groups, a 2,4,6-trihalogen-1,3,5-triazine filler component and an alkali metal halogenide filler component. The support is useful in molecular biology particularly for the fixing of biomacromolecules and for clinical and analytical detection of immunologically significant factors or organic or inorganic components of liquids.

46 Claims, No Drawings

CHEMICALLY ACTIVE TRIAZINE SUPPORT COMPOSITION

BACKGROUND OF THE INVENTION

The invention concerns macromolecular masses with chemically active filler material, processes for their production and their use.

The area of use for the masses, in particular shaped bodies prepared therefrom, is molecular biology, e.g. for capillary- and electro-blotting and for screening tests. Moreover, the material according to the present invention can be employed for the binding of microorganisms in solid phase immunoassay and as carrier for test strips.

Macromolecules with nucleophilic group can be bound with reagents which significantly increase the chemical activity of these molecules. There exist known chemically active macromolecular compounds which display for example OH—groups or $NH_2$—groups, to which cyanuric chloride can be bound. With appropriate management of the reaction, two reactive chlorine atoms of the cyanuric chloride are maintained. Both these atoms are responsible for the particular chemical activity of the macromolecule, that is a nucleophilic substitution by means of appropriate compounds is possible at these places. A process for the production of such macromolecules is described, for example, in DE-OS No. 17 68 798.

These macromolecules or other products prepared therefrom, display however an activity of the chlorine atoms which only approaches the theoretical activity. This is essentially attributed to the fact that the remaining chlorine atoms of the triazine ring are easily hydrolyzable and cross-polymerizations between the individual macromolecules occur. A further disadvantage of the covalent bonding of cyanuric chloride to a nucleophilic group of a macromolecule—with regard to preparation of a chemically active polymer—is the only limitedly available number of reactable groups.

SUMMARY OF THE INVENTION

It is therefore the aim of the present invention to be able to significantly increase the chemical activity of mixtures, respectively shaped bodies based upon triazine derivatives, composed predominantly of macromolecular material.

The invention is therefore based upon the technical object of developing a macromolecular mass based upon triazine derivatives which, by means of suitable filler material, attain a high increase in the binding capacity for biomacromolecules, microorganisms and lower-molecular compounds. This object is attained according to the present invention by means of a macromolecular mass which is composed of

- a macromolecular compound with 4,6-dihalogen-1,3,5-triazine-groupings in an amount between 1–80% by volume (I)
- 2,4,6-trihalogen-1,3,5-triazine in an amount from 0.5–50% by volume (II)
- halogenide in an amount up to 20% (III)
- a macromolecular compound in an amount from 5–80% (IV)
- with or without buffer substance up to 5% by volume (V) and
- with or without a liquid dispersing agent (VI).

The characteristics of the mass, such as mechanical and physical characteristics, are determined by the amount and type of the employed polymer and by its shaping. The chemical activity is fixed in the first place by means of the amount of the provided filler substance, such as 2,4,6-trihalogen-1,3,5-triazine (II) and the halogenide (III), and naturally likewise by means of the molding of the mass. The cyanuric halogenide is available across three active halogen atoms, which can be nucleophilically substituted. Indeed, the enormously high activity of the mass is not solely explicable by means of the increased number of active halogen atoms. It has surprisingly turned out that only the mass in its composition according to the present invention provides these high activity values. The halogenide likewise provided in the mass, particularly alkalihalogenide, serve for microfixation of the cyanuric halogenide.

In principle, all polymers (with or without nucleophilic groups) can be employed as polymer component IV, so long as they are compatible with the polymer component I and the filler substance. The same applies for the macromolecular foundation substance of polymer component I, which can, if necessary, display further nucleophilic groups. Examples of suitable polymers include cellulose, cellulose derivatives, dextran and gelatin, however also synthetic polymers with OH—and $NH_2$—groups, such as polyamide and polyvinylalcohol.

The preferably employed filler materials are cyanuric chloride (II), sodium chloride (III) and sodium acetate (V) whereby sodium acetate simultaneously acts as a buffer substance. Water-free inert solvents are particularly suitable as dispersing agent (VI).

Indeed according to the choice of starting materials and the particular management of the process, the masses according to the present invention will have either a compact or disperse form. In the case of the provision of a dispersed form, the particles can be fiber-like, sphere-shaped and/or cornered (angular). In the case of the provision of a compact form, the shaped bodies can display a sphere-shaped, laminar-shaped or cornered form.

The molding of the mass is influential insofar as the chemical activity is concerned, in that a great surface offers more places for the fixation of biomacromolecules. Accordingly, a disperse system is particularly suitable for the binding of nucleophilic reagents. Fiber-like particles can be shaped, for example, into paper, when cellulose and cellulose compounds are employed as polymer. In this case addition of another polymer, such as e.g. polyamide, can provide the paper with further mechanical stability. The mass can be provided in solid or liquid aggregate state, which is determined in the first instance by the aggregate state of the polymer portion and, on the other hand, by a liquid dispersing agent which, if necessary, also partially provides the function of a solvent.

Upon production of the mass according to the present invention and the shaped bodies thereof, one must observe that as a rule the employed filler substances (II, III, V) have to be provided in a solution. This requires a precise proportioning of the amounts of the components. The polymer components are expediently provided in dispersed condition, whereby the particle shape and the particle size will depend substantially upon the final purpose of use. However, it is possible for the polymer components also to be provided partially in dissolved form. Through adherence of the to be described fundamental process conditions for preparation of the mass and the shaped body, a simultaneous crystallization out and separation of the filler material in the polymer phase will take place.

The preparation of the mass according to the present invention can follow according to several different variations or techniques:

Variation 1

The macromolecular compound with 4,6-dihalogen-1,3,5-triazine-groupings (I) is added with thoroughly mixing in a stirring arrangement with a dispersing agent, with triazine (II), with halogenide (III) and the polymer component (IV), followed by evaporization of the dispersing agent. Thereby occurs a microcrystalline precipitation of the filler material (II, III) in the mixture, particularly on the polymer phase. The obtained mass is then washed with a dispersing agent, followed by drying and moisture-tight packing.

Variation 2

The halogenide (III) and the triazine component (II) are microcrystalline precipitated in the polymer components (I) and (IV) through addition of a suitable solvent mixture such as solvent miscible with water (alcohol, ketone, organic acid).

Variation 3

The polymer portion (IV) is added in the form of a dispersion or solution after evaporization of the dispersing agent and washing, during which intermixing the liquid phase is evaporated.

Preparation of the shaped body is effected principally in two ways:

1. The prepared mass is subjected to a shaping process by means of known technique directed essentially according to the employed polymer and the purpose of use. For example, for spinning of the mass, a spinnable polymer must be provided. The deformability of the mass is obtained by means of solvent—respectively dispersing agent—addition, which agents can, if necessary, be removed by means of drying.

2. One proceeds from already pre-shaped porous polymer bodies which have been treated with a solution that contains the triazine (II) and halogenide (III). Expediently, the treatment is performed by means of the provision of an intensive turbulence in the treatment bath. Thereby occurs a microcrystalline precipitation in the polymer phase. In this manner highly active shaped bodies with paper-like matrix can be prepared.

The masses according to the present invention, and the shaped bodies produced therefrom distinguish by an unusually high binding capacity with regard to biomacromolecules, microorganisms and lower-molecular compounds, such as dyes and leukodyes. Shaped bodies of macromolecular mass with paper-like matrix possess, for example, a binding capacity for DNA respectively RNA which lies about ten times higher than comparable papers. The binding capacity can be varied by means of the composition, whereby the maximum value lies at about 10,000 $\mu$g DNA/g mixture. This high activity is not attributable solely by the presence of covalently bound triazine, respectively free triazine, but is only effected by means of the specific mixture composition according to the present invention.

The employment of the masses according to the present invention takes place within the realm of molecular biology. Thus, for example, a surface carrier according to the present invention of cellulose basis, if necessary containing polyamide fibers, can be employed for transfer techniques (southern, northern, western techniques).

With these techniques the nucleic acids, respectively protein mixtures which are electrophoretically separated in a gel are conveyed to the surface carrier and then fixed, whereupon they are available for specific detection-reactions. The transfer of the compounds from the separation gels can be effected e.g. by means of capillary-or electro-blotting. With great advantage the materials according to the present invention can be employed for paper test strips in order to obtain a firm binding of the employed detection-reagents in the paper, so that no washing-out effects occur.

With fixed phase immunoassay one obtains excellent results based upon the high loading capacity of the shaped bodies, such as surface carriers, prepared from the mass:

by means of the binding of antigens respectively antibodies in the shaped body according to the present invention, substantially higher loading densities can be obtained, by means of the mobilization, no desorption of the immune reactants occurs during the necessary incubation and washing operations of an immunoassay. Accordingly, so-called method errors are considerably reduced.

The employment of the materials according to the present invention leads to a considerable reduction in the costs of clinical practice. On the one hand, the plastic materials utilized as 1-way containers are replaced; on the other hand, the occasionally very valuable and expensive proteins are saved. By means of the immobilization of the antigens, respectively antibodies in the shaped bodies according to the present invention, a new aspect is reached in the preparation of easy to handle and standardized test kits for commercial production.

The carrier materials according to the present invention are moreover suitable for the fixation of microorganisms, whereby in surprising manner the viability and germinating potential of the objects remains maintained. A further important use of the carrier material, by utilization of its high binding capacity, is the possibility of screening substances from unpurified biological samples such as e.g. the detection of viral ribonucleic acids, free viral nucleic acids (RNA) and replicative forms of the virus-RNA, viroids and virusoids in extracts recovered from plant or other materials or fluids by means of the binding of the RNA to be detected to the surface carrier according to the present invention and subsequent hybridization by means of marked complementary deoxyribonucleic acid (cDNA), cloned cDNA (recombinant-cDNA), double-strand RNA (dsRNA), single-strand virion-RNA (ssRNA) or complementary RNA (cRNA) and the RNA replicative intermediate as molecular hybridization probe.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

A mixture of 10 volume parts cellulose fibers and 70 volume parts cellulose fibers with dichlorotriazine groupings is stirred in a stirring apparatus with a mixture of a saturated Koch's salt solution (9 volume parts NaCl) in water and a solution of 11 volume parts cyanuric chloride in acetone. After addition of acetic acid, the solvent is evaporated in a vacuum so that a microcrystalline precipitation of the mixture occurs on the cellulose fibers. By means of stirring during the crystallization, the crystallization is accelerated whereby relatively smaller crystals are formed.

The crystals can be made visible by scanning electron microscopy and possess a size up to 100 $\mu$m, the size of the crystals being variable by means of the crystallization conditions, with optimal size lying between about 1 and 10 $\mu$m. After termination of the crystallization process the cellulose fibers are washed 2×10 minutes with acetone and then dried in a vacuum. For secure storage and for further working up into shaped bodies, the obtained mixture can be dispersed in water-free dioxane. It displays a DNA-binding capacity of about 10,000 $\mu$g DNA/g.

The DNA-binding test is performed in the following manner:

A determined amount of the active mixture, respectively determined surface of shaped body is incubated overnight in a phosphate buffer pH 5.5 with an excess of radioactively marked, denaturated, sonicated DNA. After washing with water, the bound amount of DNA is determined by means of measuring the radioactivity of the carrier. The DNA-binding capacity is given relative to g of the mixture respectively cm$^2$ of the shaped body.

EXAMPLE 2

A mixture of polyamide fibers and polyamide fibers with dichlorotriazine groupings is stirred in a stirring apparatus with a mixture of a saturated Koch's salt solution in water and a solution of cyanuric bromide in acetone. The further working up follows as described in Example 1.

EXAMPLE 3

A mixture of polyurethane (powder of fibers) and cellulose fibers with dichlorotriazine groupings is stirred in a stirring apparatus with a mixture of a saturated Koch's salt solution and a cyanuric chloride solution in acetone. Further working up follows in a manner described in Example 1.

EXAMPLE 4

A mixture of DEAE cellulose fibers and cellulose fibers with dichlorotriazine groupings is stirred in a stirring apparatus with a mixture of a saturated Koch's salt solution in water and in a solution of cyanuric chloride in acetone. The further working up is effected in the manner as described in Example 1.

EXAMPLE 5

A mixture of gelatin and cellulose particles with dichlorotriazine groupings is stirred in a stirring vessel with a mixture of a saturated sodium chloride solution in water and a solution of cyanuric chloride in acetone. Further working up is performed in a manner as described in Example 1.

EXAMPLE 6

A mixture of polyvinylalcohol and cellulose fibers with diclorotriazine groupings is stirred in stirrer means with a mixture of a saturated sodium chloride solution in water and a solution of cyanuric chloride in acetone. Further working up is effected in the manner as described in Example 1.

EXAMPLE 7

A mixture of cellulose fibers and cellulose fibers with dichlorotriazine groupings is stirred in a stirrer vessel with a mixture of a saturated sodium chloride solution in water and a solution of cyanuric chloride in acetone. After addition of acetic acid and 0.5% by volume sodium acetate (calculated with regard to the total mixture preparation) the solvent is evaporated off. Further working up follows according to Example 1.

EXAMPLE 8

Cellulose fibers with dichlorotriazine groupings are treated as described in Example 1 with Koch's salt and cyanuric chloride solution. The obtained mixture is subsequently dispersed in dioxane/polyvinylchloride (molecular weight 30,000) solution and worked up into a flat, paper-like shaped body.

EXAMPLE 9

Filter lamina of cellulose are activated with cyanuric chloride according to known technique, e.g. after 15 minutes treatment with 3N NaOH the filters are intermediately dried and then activated for 10 minutes in a solution of 5% cyanuric chloride in dioxane/xylene (1:1).

After completion of the activation, a microcrystalline precipitation of NaCl and the triazine component is obtained by means of addition of a mixture of 70-80% acetone and acetic acid.

The filter lamina are subsequently washed with acetone 2×10 minutes and then dried. The DNA-binding capacity of the filter lamina amounts to 200 $\mu$g/cm$^2$.

EXAMPLE 10

Filter lamina of cellulose are activated with cyanuric chloride as described in Example 9. After completion of the activation, a microcrystalline precipitation of NaCl and the triazine component is obtained by means of addition of a mixture of butanol/acetone/glacial acetic acid (50:30:20).

The filter lamina are subsequently washed with acetone 2×10 minutes and then dried.

EXAMPLE 11

Filter lamina of cellulose are activated with cyanuric chloride as described in Example 9. After the activation, the filters are agitated in an acetic acid solution of cyanuric chloride and NaCl in an acetone/H$_2$O mixture, and the solvent is evaporated under vacuum. The filters are subsequently washed with acetone 2×10 minutes, if necessary, and then dried.

EXAMPLE 12

A surface carrier with paper-like matrix according to the present invention is cut into squares measuring 4×4 cm size. Each sheet area is treated dropwise with 5 $\mu$l buffer (0.1M phosphate 0.9% NaCl) having different dilutions of *Bacillus subtilis* (168M) in orderly sequence as follows:

Dilution 1 = 100,000 germs
2 = 10,000 germs
3 = 1,000 germs
4 = 100 germs
5 = 10 germs

| |
|---|
| 6 = 1 germ |

Phosphate buffer having pH range 5–8 are tested therewith. As control, the analogous applications are conducted on normal filter paper. After the applications an incubation is effected for a period between 10 and 20 minutes at room temperature. Thereupon the carrier is placed on a fritted funnel with the drop application side facing downwardly and then washed with 10 ml phosphate buffer, pH 7.6.

Subsequently the carrier is placed with the drop application side facing upwardly in petri dish containing agar and coated over with 10 ml so-called soft agar at 42° C. (9 cm petri dish; glucose-bouillon agar, pH 7.2±0.2). An incubation is then effected at 37° C. in a microbiological incubator. After 36 hours a colony growth is evident at the drop sites.

The control paper displays colony growth *only* at pH 7.0 up to dilution 3, whereas the employed surface carrier shows colony growth at pH 6.5 up to dilution 4. At pH 7.0, the surface carrier displays a colony growth up to dilution 6. At pH 7.6, the surface carrier displays colony growth only at dilution 1.

These results indicate that the surface carrier displays a complete binding with full viability at pH 7.0. The binding is increased at least 1000 times relative to the control paper at pH between 6.5–7.0.

EXAMPLE 13

A surface carrier with paper-like matrix according to the present invention is reacted with human immunoglobulin G, radioactively labelled with $I^{125}$, in different concentrations and with various buffer systems, followed by incubation for 16 hours at a temperature of 37° C. After 3 washings with PBS-buffer, pH 7.4, which contains 0.05% Tween 20, the possibly still excess reactive groups are blocked with 1 ml ethanolamine solution. After renewed washing with the above-mentioned PBS buffer the bound amount of protein is determined by means of measurement of the radioactivity. In order to determine possible desorption, the samples are subsequently washed again 7 times with PBS-buffer. The so loaded surface carriers are thereafter reacted with a conjugate composed of a canine-antihuman IgG and the enzyme alkaline phosphatase, and are then incubated overnight at room temperature for determination of the immunoreactivity. After an additional washing, the enzyme activity of the alkaline phosphatase is determined by means of hydrolysis by 4-nitrophenylphosphate in 0.5 ml diethanolamine buffer, pH 9.8, and photometrical measurement of the enzyme product at 405 nm after stoppage with 1 n NaOH. After performance of the enzyme immunoassay, the surface carriers are washed twice, each time with 0.5 ml PBS-buffer and subsequently reacted with one of the following disassociation reagents for 1 hour at a temperature of 4° C.: (1) PBS-buffer 2 m in NaCl, containing 5% dioxane; (2) 1 m KSCN; (3) 3 m KSCN; (4) 4.5 m MgCl; (5) 1 m NaI; (6) HCl-glycine buffer, pH 2.8. By means of any or all of these agents, the bound antigen-antibody complexes are split off, so that the surface carriers loaded with human IgG can be employed again for enzyme immunoassay.

EXAMPLE 14

Flat-shaped bodies according to the present invention ($A = 56$ mm$^2$) are loaded with human factor VIII in the manner described in Example 13. These carriers ae then transferred into polystyrene-microtitration plates or polystyrene tubes, and conducted in the described type and manner in the following enzyme immunoassay for determination of F VIII-related-antigen (263; W. Schossler, M. Stepanauskas, Chr. Dittrich: Acta biol. med. germ. 41 (1982) 695). For this purpose the shaped bodies are reacted with an incubation mixture composed of the plasma to be determined and a canine-antihuman factor VIII-antibody provided in excess, followed by incubation for a period of 6 hours at a temperature of 37° C. After a washing with PBS-buffer, pH 7.4, containing 0.05% Tween 20,200 µl of a conjugate composed of a wether-anti-canine-IgG and the enzyme alkaline phosphatase are added. Finally, after several hours incubation and further washing out, the enzyme activity is determined in the manner described in Example 13. The splitting off of the bound antibody or antibodies follows with one of the disassociation reagents cited in Example 13, so that the carrier, loaded with factor VIII can be employed anew in immunoassay.

EXAMPLE 15

A surface carrier according to the present invention with paper-like matrix is loaded with human factor VIII in the manner described in Example 14. This carrier serves as a model for screening tests of (monoclonal) antibody. After performance of the washing operation, which is effected in particularly simple manner with these surface carriers, the substances to be tested and to be determined are applied in dots with a suitable application piston. In this case suitable dilutions of a canine-anithuman-factor VIII-anti serum, serve as antibody source and a canine serum as negative control serves respectively. After an incubation period of 4–6 hours at a temperature of 37° C., the surface carrier is washed again and then further incubated for a period of 4 hours at 37° C. or overnight at room temperature with a sheep-anti-canine-IgG, coupled with the enzyme peroxidase. The samples are then multiply washed, after which the enzyme activity is determined with a suitable detection system, thus e.g. 4 mM O-phenylenediamine and 1.5 mM $H_2O_2$ by means of visual evaluation of the produced coloration. A positive coloration indicates undoubtedly the presence of an antibody.

EXAMPLE 16

Determination of tobacco rattle virus (TRV) with recombinant-cDNA in potatoes (a)

0.5 g plant material is homogenized in a mortar under addition of 0.5 ml 0.1M tris-HCl (pH 7.5), and the homogenate is centrifuged in a table centrifuge, e.g. TH 12, VEB Zentrifugenbau Engelsdorf, in 1.5 ml centrifugation tubes (according to Eppendorf). 250 µl of the upper centrifuged layer are mixed with 250 µl of a mixture of 1 part phenol with 0.1% 8-hydroxyquinoline, equilibrated with 0.1M tris-HCl (pH 7.5), 1 part chloroform mixture (24 parts chloroform: 1 part isoamyl alcohol), enriched with 1% SDS, and then, after powerful agitation, heated for 5 minutes at 65° C. After division of the phases by means of centrifugation, the aqueous phase is withdrawn, and agitated twice with chloroform mixture, then brought to a final concentration of 0.3M sodium acetate, and mixed with 3 volumes of 96% alcohol. The RNA is precipitated by 10 minutes' cooling of the test tubes to −70° C. The alcohol is subsequently evacuated in a vacuum, after which the sample is rewashed with 70% alcohol. Then, after drying off the alcohol the sample is taken up in 4 μl distilled water. The sample is brought to a final concentration of 1M glyoxal, 50% DMSO and 10 in M sodium-phosphate (pH 7.0) in 16 μl total volume, and the RNA is denatured 1 hour at 50° C. with subsequent chilling in an ice bath. 1 μl of the denatured sample is applied to the surface carrier by means of a microliter pipette. After the application of all samples, inclusive of samples of healthy control plants, the material is fixed for a period of 1 hour at room temperature. The saturation of the free binding capacity of the paper follows by means of treatment with 10% ethanolamine pH 7.0. Then follows a pre-hybridization of the loaded carrier in a solution of 50% formamide, 5-fold Denhardts buffer, 0.1% SDS and 5-fold SSPE under addition of 100 μg/ml pre-hybridization solution denatured non-specific DNA at a temperature of 42° C. After 18 hours the solution is exchanged against a solution composed of 50% formamide, 2-fold Denhardt-buffer, 0.1% SDS, 5-fold SSPE and 100 μg/ml hybridization solution denatured non-specific DNA. This solution likewise contains 1 μg $P^{32}$-labelled recombinant-TRV-cDNA (activity about 0.25 MB). After the hybridization, the surface carrier is washed 4 times at room temperature, each time for a period of 30 minutes in a solution of 3×SSC and 0.1% SDS, then air-dried and autoradiographed 2–5 days. The evaluation of the X-ray film follows visually or, after cutting of the film into strips, with an extinction registering apparatus.

Detection of barley stripe mosaic virus (BSMV) in barley with cDNA (b)

The preparation of the samples follows in the manner described under (a). The virus-RNA is denatured by means of redissolving of the sample precipitated in alcohol in a final volume of 10 μl, containing 1M glyoxal and 10 mM sodium phosphate (pH 7.0), 1 hours' heating at 50° C. and subsequent chilling at 0° C. The hybridization, washing and evaluation follow as described under (a). The molecular probe is, however, obtained as follows: to the isolated RNA of BSMV a reverse transcript is produced with the aid of AMV-reverse transcriptase oligo-dT as primer and $P^{32}$ labelled α-deoxyribonucleotide triphosphates. It can be employed for the hybridization.

EXAMPLE 17 a. pH test strips

The surface carrier is soaked with a solution of 10 mg methyl red and 30 mg bromothyinol blue/100 ml ethanol and then dried. Subsequently the paper is cut into vertical strips of 0.5 cm width and adhered to plastic foil. These are then cut into 0.5 cm wide strips so that a reaction zone measuring 0.5×0.5 cm is present on each test strip.

b. Test strips for detection of leukocytes in urine

A surface carrier is impregnated with 0.1M phosphate-buffer (pH 8.0) and 2 mM EDTA. After drying follows a second soaking, with a solution of 35 mg indoxylacetate in 100 ml acetone. The preparation of the test strips follows as described under a.

c. Test strips for detection of nitrite in urine

The surface carrier is impregnated with 0.5M citric acid having a pH value of 1.6. After drying follows a second soaking, with 5 mM sulfanilic acid amide and 0.5 m M N-(1-naphthyl)-ethylenediamine dihydrochloride in acetone. The preparation of the test strips follows as described under a.

d. Test strips for detection of reducing compounds in urine.

The surface carrier is impregnated with a solution of 125 mg 2,6-dichlorophenol indophenol in 100 ml Sorensen-phosphate-buffer having a pH value of 7.0. Production of the test strips follows in the manner described above under a.

It will be understood that each of the elements described above, or two or more together, may also find a useful application for other problems of molecular biology, testing differing from the types described above.

While the invention has been illustrated and described as embodied in macromolecular masses with chemically active filler material, processes for their production and uses thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A composition with chemically active filler components comprising
   (a) a polymer compound having no triazine groups in a concentration of 5–80% by volume;
   (b) a polymer compound with 4,6-dihalogen-1,3,5-triazine groups in a concentration of 1–80% by volume; ,p1 (c) a 2,4,6-trihalogen-1,3,5-triazine filler component in a concentration of 0.5–50% by volume; and
   (d) an alkali metal halogenide filler component in a concentration of 0.1–20% by volume.

2. The composition according to claim 1, wherein the polymer compound contains nucleophilic groups.

3. The composition according to claim 1, wherein the polymer compound has no nucleophilic groups.

4. The composition according to claim 1, wherein the polymer compound with 4,6-dihalogen-1,3,5-triazine groups is a polymer which is completely substituted by 2,4,6-trihalogen-1,3,5-triazine compounds.

5. The composition according to claim 1, wherein the polymer compound is a natural polymer.

6. The composition according to claim 5, wherein the natural polymer is cellulose, a cellulose derivative or gelatin.

7. The composition according to claim 2, wherein the polymer compound is a synthetic polymer having hydroxyl or amino groups.

8. The composition according to claim 7, wherein said synthetic polymer is a polyamide or a polyvinyl alcohol.

9. The composition according to claim 1, wherein the composition contains buffering substances selected from the group consisting of acetates and phosphates.

10. The composition according to claim 9, wherein the buffering substances are selected from the group consisting of sodium acetate, and sodium phosphate.

11. The composition according to claim 1, wherein said composition comprises a dispersed system.

12. The composition according to claim 11, wherein the dispersed system is composed of particles having a fibrous, spherical or cornered shape.

13. The composition according to claim 1, in the form of a shaped body.

14. The composition according to claim 13, wherein the shape is spherical, laminar or cornered.

15. The composition according to claim 11, containing an inert organic solvent as a dispersing agent.

16. The composition according to claim 13, wherein the shaped body is in the form of a spun fiber.

17. The composition according to claim 1, wherein the polymer compound is a binding agent.

18. The composition according to claim 13, wherein the shaped body is in the shape of paper.

19. The composition according to claim 1, wherein the halogen of the 2,4,6-trihalogen-1,3,5-triazine is chlorine or bromine.

20. Process for preparing a composition with chemically active fillers, comprising:
forming a mixture of a polymer compound having no triazine groups in a concentration of 5-80% by volume and a polymer compound with 4,6-dihalogen-1,3,5-triazine groups in a concentration of 1-80% by volume with a liquid phase containing a dispersing agent, 2,4,6-trihalogen-1,3,5-triazine and an alkali metal halogenide.

21. The process of claim 20, further comprising adding suitable solvent and dispersing agent to the mixture and then removing said dispersing agent and said solvent.

22. The process according to claim 20, wherein the polymer compound contains nucleophilic groups.

23. The process according to claim 20, wherein the polymer compound has no nucleophilic groups.

24. The process according to claim 22, wherein the polymer compound is a natural polymer.

25. The process according to claim 24, wherein the natural polymer is cellulose, a cellulose derivative or gelatin.

26. The process according to claim 22, wherein the polymer compound is a synthetic polymer having hydroxyl or amino groups.

27. The process according to claim 26, wherein the synthetic polymer is polyvinyl alcohol or polyamide.

28. The process accordign to claim 20, wherein the mixture contains a dispersing agent and said dispering agent is an inert liquid organic compound not being able to dissolve the polymer compound.

29. The process according to claim 28, wherein the dispersing agent is selected from the group consisting of alcohols, ethers and ketones.

30. The process according to claim 29, wherein the dispersing agent is dioxane or acetone.

31. The process according to claim 20, wherein the mixture contains a solvent and the solvent is an organic liquid miscible with water.

32. The process according to claim 31, wherein the solvent is selected from the group consisting of alcohols, ketones, organic liquid acids and cyclic ethers.

33. The process according to claim 20, wherein the mixture contains a buffering substance selected from the group consisting of alkali metal acetates and phosphates.

34. The process according to claim 33, wherein the buffering substance is sodium acetate, or sodium phosphate.

35. The process according to claim 20, wherein the halogen of the 2,4,6-trihalogen-1,3,5-triazine is chlorine or bromine.

36. The process according to claim 20, wherein the proportion of organic solvent is 50-90% by volume and the difference to 100% is acetic acid.

37. Method for the fixation of cells to a support material comprising:
(a) contacting the cells with a support having chemically active filler components composed of:
(i) cellulose and/or cellulose derivative having no triazine groups in a concentration of 5-80% by volume;
(ii) cellulose and/or cellulose derivative with 4,6-dihalogen-1,3,5-triazine groups in a concentration of 1-80% by volume;
(iii) a 2,4,6-trihalogen-1,3,5-triazine filler component in a concentration of 0.5-50% by volume; and
(iv) an alkali metal halogenide filler component in a concentration of 0.1-20% by volume to form a conjugate of support and cells; and
(b) washing said conjugate of support and cells.

38. Method for solid phase immunoassay to immunologically determine the presence of antigens or antibodies, comprising fixing antibody or antigen to a cellulose-containing support as a solid phase, carrying out an immunoreaction, to form an antigen-antibody complexe containing an antigen or antibody being determined, determining the presence of the antigen or antibody and, cleaving the formed antigen-antibody complexe from the support to allow repeat use of the loaded solid phase in said immunoassay, said cellulose-containing support being composed of:
(a) cellulose or a cellulose derivative, having no triazine groups in a concentration of 5-80% by volume;
(b) cellulose or cellulose derivative with 4,6-dihalogen-1,3,5-triazine groups in a concentration of 1-80% by volume;
(c) a 2,4,6-trihalogen-1,3,5-triazine filler component in a concentration of 0.5-50% by volume; and
(d) an alkali metal halogenide filler component in a concentration of 0.1-20% by volume.

39. The method according to claim 38, wherein the support is in the form of a sphere, semisphere, cube, cylinder or sheet.

40. The method according to claim 38, wherein the support is a hollow body being open or closed and having a volume between 0.01 cm$^3$ and 15 cm$^3$.

41. The method according to claim 38, wherein the cellulose or cellulose derivative is provided as fibrous particles.

42. The method according to claim 39, wherein the sheet has the shape of paper.

43. Method for the detection of the RNA of plant viruses, viroids or virusoids comprising contacting a plant extract with a support material composed of:
(a) cellulose or a cellulose derivative having no triazine groups in a concentration of 5-80% by volume;
(b) cellulose or a cellulose derivative with 4,6-dihalogen-1,3,5-triazine groups in a concentration of 1-80% by volume;
(c) a 2,4,6-trihalogen-1,3,5-triazine filler component in a concentration of 0.5%-50% volume; and
(d) an alkali metal halogenide in a concentration of 0.1-20% by volume; and detecting RNA bound to the support.

44. The method according to claim 43, wherein the support is in the form of a sheet.

45. The method according to claim 44, wherein the sheet is in the form of paper.

46. A method for detecting organic and inorganic components in liquids, comprising contacting a liquid with a test strip composed of:
(a) cellulose or a cellulose derivative having no triazine groups in a concentration of 5–80% by volume;
(b) cellulose or a cellulose derivative having 4,6-dihalogen-1,3,5-triazine groups in a concentration of 1–80% by volume;
(c) a 2,4,6-trihalogen-1,3,5-triazine filler component in a concentration of 0.5–50% by volume; and
(d) an alkali metal halogenide filler component in a concentration of 0.1–20% by volume; and detecting organic and inorganic components bound to the test strip.

* * * * *